United States Patent
Clancy et al.

(10) Patent No.: US 7,670,626 B2
(45) Date of Patent: Mar. 2, 2010

(54) DELIVERY OF A BIOACTIVE MATERIAL

(75) Inventors: Maurice Joseph Anthony Clancy, Cellbridge (IE); K. Iain Cumming, Dublin (IE); Conor B. McCrystal, Dublin (IE)

(73) Assignee: Merrion Research III Limited, Dublin 2 (IE)

( * ) Notice: Subject to any disclaimer, the term of this patent is extended or adjusted under 35 U.S.C. 154(b) by 1186 days.

(21) Appl. No.: 10/482,081

(22) PCT Filed: Jul. 2, 2002

(86) PCT No.: PCT/IB02/03651

§ 371 (c)(1),
(2), (4) Date: Dec. 22, 2003

(87) PCT Pub. No.: WO03/003999

PCT Pub. Date: Jan. 16, 2003

(65) Prior Publication Data

US 2004/0176328 A1    Sep. 9, 2004

Related U.S. Application Data

(60) Provisional application No. 60/302,540, filed on Jul. 2, 2001.

(51) Int. Cl.
*A61K 9/16* (2006.01)
*A61K 9/20* (2006.01)
*A61K 9/48* (2006.01)

(52) U.S. Cl. ............... 424/490; 424/451; 424/464; 424/489; 424/491

(58) Field of Classification Search ............ None
See application file for complete search history.

(56) References Cited

U.S. PATENT DOCUMENTS

| | | | |
|---|---|---|---|
| 4,450,877 A | 5/1984 | Walker et al. | 141/1 |
| 5,281,420 A * | 1/1994 | Kelm et al. | 424/452 |
| 5,525,355 A | 6/1996 | Brown et al. | |
| 5,776,495 A | 7/1998 | Dulclos et al. | 424/455 |
| 6,248,363 B1 * | 6/2001 | Patel et al. | 424/497 |
| 6,372,728 B1 | 4/2002 | Ungell | 514/109 |
| 6,468,559 B1 * | 10/2002 | Chen et al. | 424/451 |
| 6,689,823 B1 * | 2/2004 | Bellare et al. | 523/115 |
| 2003/0091623 A1 * | 5/2003 | Cumming et al. | 424/465 |

FOREIGN PATENT DOCUMENTS

| | | |
|---|---|---|
| EP | 0 642 786 A | 3/1995 |
| EP | 0642786 A1 * | 3/1995 |
| WO | WO 97/05903 A | 2/1997 |
| WO | WO 97/08903 | 3/1997 |
| WO | WO 99/18972 A | 4/1999 |
| WO | WO 9918972 A1 * | 4/1999 |
| WO | WO 00/00179 A | 1/2000 |
| WO | WO 00/61111 A | 10/2000 |
| WO | WO 0061111 A1 * | 10/2000 |
| WO | WO 01/37808 A | 5/2001 |
| WO | WO 01/82903 A | 11/2001 |

* cited by examiner

*Primary Examiner*—S. Tran
(74) *Attorney, Agent, or Firm*—Myers, Bigel, Sibley & Sajovec, P.A.

(57) ABSTRACT

A solid pharmaceutical composition comprising a water-soluble bioactive material and an encapsulating material which is present in the composition in the form of continuous solid phase, and in which solid particles of the bioactive material are dispersed and encapsulated in the continuous solid phase of the encapsulating material, wherein each of the bioactive material and the encapsulating material is normally a solid at room temperature and the melting point of the encapsulating material is lower than the melting point of the bioactive material, the bioactive material being preferably a bisphosphonate, most preferably alendronate, and the encapsulating material includes an enhancer, preferably a mono- or di-glyceride, or an encapsulating surfactant, preferably, a polyoxyethylene/polyoxypropylene block copolymer having surface active properties, and a process for preparing the composition in which solid particles of the bioactive material are mixed with and dispersed in the encapsulating material which is in molten (liquid) form; and cooling the molten form of the encapsulating material to form a solid pharmaceutical composition having the solid particles of the bioactive material dispersed and encapsulated in a continuous solid phase of the encapsulating material.

5 Claims, No Drawings

DELIVERY OF A BIOACTIVE MATERIAL

CROSS-REFERENCE TO RELATED APPLICATIONS

This application is the U.S. national stage application of International Application No. PCT/IB02/03651, filed Jul. 2, 2002 which is based on and claims the priority of U.S. Application No. 60/302,540, filed Jul. 2, 2001.

FIELD OF THE INVENTION

The present invention relates to a composition that contains a bioactive material that can be ingested orally by an individual. More specifically, the present invention relates to a pharmaceutical composition, which upon being ingested orally by an individual, exhibits improvements in the absorption of the bioactive material in the gastrointestinal tract of the individual.

The present invention will be described initially in connection with its applicability to the use of alendronate which belongs to a well known class of pharmaceuticals known as bisphosphonates. However, the present invention has wider applicability as will be evident from the detailed description of the invention which is set forth below.

Alendronate, as well as other bisphosphonates, are drugs which are useful in inhibiting bone resorption and in treating medical conditions which are associated therewith, for example, osteoporosis. Unfortunately, alendornate (as well as many other drugs) have low bioavailability when ingested orally by an individual, that is, the alendronate is absorbed poorly in the gastrointernal tract of the individual, as described more fully below.

The present invention relates to means for improving the bioavailability of alendronate and other drugs upon ingestion orally by an individual.

REPORTED DEVELOPMENTS

U.S. Pat. No. 6,372,728 describes an oral dosage form of a pharmaceutical composition that contains a bisphosphonate, for example, alendronate, and an enhancer which functions to improve (enhance) the bioavailability of the bisphosphonate. The enhancer is described as medium chain glyceride or a mixture of medium chain glycerides. The composition can include also a surface active agent, for example, a surfactant sold under the trademark Tween. The '728 patent discloses that the oral dosage form of the composition is a saline solution having a pH of between 1 and 11, preferably between 3 and 8. Unfortunately, compositions described in the '728 patent are unstable in storage as manifested by precipitation of the bisphosphonate in the composition.

Published International Application bearing Publication No. WO 97/08903 discloses a pharmaceutical composition comprising a polar drug, for example, a bisphosphonate, and an enhancer which comprises (a) a mixture of a fatty acid having 6 to 16 carbon atoms or a salt thereof and a dispersing agent or (b) a mixture of mono/diglycerides of medium chain fatty acids and a dispersing agent and also means adapted to release the polar drug and enhancer in the colon. The "dispersing agent" is described as a material that is able to position itself at the interphase between the formulation phase and the aqueous phase in the colon and thereby reduce the interfacial tension between two phases and promote the dispersion of the formulation in the lumen of the colon. Examples of dispersing agents include polyglycolyzed glycerides, polyoxyethylene sorbitan fatty acid esters, and polyoxyethylene (4) sorbitan monolaurate.

In order to ensure delivery of the drug to the proximal colon of the individual, the pharmaceutical composition includes means to prevent release of the polar drug and enhancer until the composition reaches the colon, preferably the proximal colon. Such means consists of a coating that is provided on the capsule, tablet or pellet comprising the composition to prevent release until the tablet, capsule or pellet reaches the proximal colon.

The aforementioned published International Application states that the composition is in the form of a liquid or semi-solid. Such compositions, like the composition described in the aforementioned '728 patent, suffer also from the disadvantage that the composition is not stable in storage.

The present invention provides, among other things, an improved stable composition which contains a bioactive material and has good bioavailability when ingested orally.

SUMMARY OF THE INVENTION

One aspect of the present invention is the provision of a solid pharmaceutical composition comprising a water-soluble bioactive material and an encapsulating material which is present in the composition in the form of continuous solid phase, and in which solid particles of the bioactive material are dispersed and encapsulated in the continuous solid phase of the encapsulating material, wherein each of the bioactive material and the encapsulating material is normally a solid at room temperature and the melting point of the encapsulating material is lower than the melting point of the bioactive material. Typically, the bioactive material is a material which has low bioavailability when administered orally to humans. Preferably, the bioactive material is a bisphosphonate, most preferably alendronate, and the encapsulating material includes an enhancer or an encapsulating surfactant, preferably, a polyoxyethylene/polyoxypropylene block copolymer having surface active properties. A preferred enhancer is a mono- or di-glyceride of a medium chain fatty acid. The composition is characterized by rapid onset of release of the bioactive material when contacted with water. In storage, the composition is stable.

Another aspect of the present invention is the provision of a process in which: (A) solid particles of a water-soluble bioactive material which is normally a solid at room temperature and which has a predetermined melting point are mixed with and dispersed in a encapsulating material which is in molten (liquid) form, the encapsulating material being normally a solid at room temperature and having a melting point lower than the melting point of the bioactive material; and (B) cooling the molten form of the encapsulating material having dispersed therein said solid particles of bioactive material to form a solid pharmaceutical composition having the solid particles of bioactive material dispersed and encapsulated in a continuous solid phase of the encapsulating material.

In yet another aspect of the present invention, there is provided a process for forming a pharmaceutical composition in a capsule by: (A) preparing a mixture comprising a liquid encapsulating material having dispersed therein solid particles of a water-soluble bioactive material which is normally a solid at room temperature, the encapsulating material being normally a solid at room temperature, and the mixture having a temperature which is sufficiently high to melt the encapsulating material, but not the solid particles of bioactive material; (B) filling a capsule with the mixture; and (C) cooling the capsule having the mixture therein to form in the capsule a solid pharmaceutical composition having the solid particles of bioactive material dispersed and encapsulated in a continuous solid phase of the encapsulating material.

Still another aspect of the present invention is the provision of a method for supplying therapeutic amounts of a bioactive material to the serum of an animal through the animal's gastrointestinal tract by oral administration of a composition of the present invention.

In preferred form, the method aspects of the present invention involve the use of bisphosphonate, more preferably alendronate, as the bioactive material, including its use to retard bone resorption in the prevention and treatment of osteoporosis and Paget's disease. Also in preferred form, the method aspects of the present invention involve an encapsulating agent which is either (A) an enhancer, preferably a mono or diglyceride of caprylic acid, a mono or diglyceride of capric acid, or a mono or di-glyceride of a mixture of capric and caprylic acids, or a mixture thereof, or (B) an encapsulating surfactant, preferably a polyoxyethylene/polyoxypropylene block copolymer having surface active properties.

Principal advantages of the present invention are that it permits the incorporation in a pharmaceutical composition of a therapeutic amount of a solid bioactive material in a form that facilitates rapid absorption when presented to the gastrointestinal tract of an animal and the composition in storage is stable.

DETAILED DESCRIPTION OF THE INVENTION

As mentioned above, the composition of the present invention includes a water-soluble bioactive material and an encapsulating material; in addition, the composition includes other ingredients that are optional. The composition can be packaged in various ways for oral administration to the body of an animal, typically, a human. A description of constituents that can comprise the composition of the present invention and the use thereof follows.

The Bioactive Material

The bioactive material (also referred to herein as "active agent") for use in the composition of the present invention is any substance which can be introduced into an animal's biological system via absorption from the gastrointestinal tract of the animal and which, upon absorption, elicits in the animal a therapeutic, prophylactic or diagnostic response. The bioactive material is typically water-soluble, that is, the bioactive material has a solubility in pure water of at least about 1 mg/ml at 20° C.

It will be evident from the description which follows that the bioactive material can be selected from a wide variety of classes of compounds, including, for example, peptides, polypeptides, polysaccharides, nucleic acids, for example, DNA and RNA, and also compounds which are representative of traditional types of drugs. It will be evident also from the following description that compositions within the scope of the present invention can be formulated to treat a vast and varied number of conditions.

Examples of drugs that can be used in the composition of the present invention are water-soluble drugs which are characterized by having low bioavailability when administered orally, for example: anticoagulants, for example, heparin or its derivatives; antimicrobials, for example, penicillin G, carbenicillin, methicillin and other poorly absorbed penicillin derivatives; cephalosporins, for example, cephalothin, cefoxitin, cefotaxime and other molecules in this series normally administered by injection; antineoplastic drugs, for example, fluorouracil, cytarabine, azauridine, vinblastine, vincristine, and bleomycin; anti-inflammatories, for example, aurothioglucose and gold sodium thiomalate; and antiparasitic drugs, for example, suramin.

Examples of other active agents that can comprise the composition include RGD peptides, hematoregulatory peptides, vasopressin, collagenase inhibitors, angiotensin inhibitors, mammalian growth hormones, erythropoietins, interleukins (for example, IL-2, 3, 4 and the like), clotting factors (for example, factors VII, VIII, IX), colony-stimulating factors (for example, G-CSF, GM-CS, M-CSF), hypothalamic-releasing peptides (for example, growth hormone-releasing peptides and gonadotropin-releasing factors), interferons, tissue plasminogen activators, atrial natriuretic peptides, tumor necrosis factor, antibodies, antibody fragments, clotting factors, dismutases, vaccines, immunoregulators, HIV protease inhibitors, neurotrophic factors (for example, nerve-growth factors), peptide and protein mimetics, and angiotensin II antagonists.

The bioactive material can comprise also small peptides (from about 2 to about 10, more preferably from about 2 to about 6, amino acid moieties). Examples include fibrinogen-receptor antagonists (RGD-containing peptides) which are tetrapeptides having an average molecular weight of about 600.

Examples of larger peptides/polypeptides that can be used in the practice of the present invention are those disclosed in Pierschbacher et al., U.S. Pat. No. 4,589,881 (>30 residues); Bittle et al., U.S. Pat. No. 4,544,500 (20-30 residues); and Dimarche et al., EP 0 204 480 (>34 residues).

There can be used also in the composition of the present invention growth hormone-releasing peptides, which are peptides generally of about twelve amino acids or less and which effect the release of growth hormone. Exemplary growth hormone-releasing peptides are the peptide His-D-Trp-Ala-D-Phe-Lys-$NH_2$ and other peptides which cause the release of growth hormone by essentially the same mechanism as His-D-Trp-Ala-Trp-D-Phe-Lys-$NH_2$. Another example of a "growth" peptide is Ala-His-D-Nal-Ala-Trp-D-Phe-Lys-$NH_2$. Growth hormone-releasing peptides are disclosed, for example, in the following U.S. Pat. Nos. 4,411,890; 4,410,513; 4,410,512; 4,228,158; 4,228,157; 4,228,156; 4,228,155; 4,226,857; 4,224,316; 4,223,021; 4,223,020; 4,223,019; 4,880,778; 4,880,777; and 4,839,344. See also: WO 89/10933 (PCT/US89/01829); Bowers et al., EP-A 398 961; and Bowers et al. EP-A 400 051.

Additional examples of a bioactive material are immunogens which can be incorporated into vaccine adjuvant systems. Examples of suitable immunogens include purified proteins and peptides and derivatives thereof.

Examples of other bioactive materials that may comprise the composition of the present development are oligosaccharides or polysaccharides, low-molecular weight heparins, fondaparinux sodium, and idraparinux sodium. Additional examples of bioactive materials include insulin, luteinising hormone-releasing hormone, leuprolide acetate, abarelix, goserelin, naferelin, buserelin, vasopressin, desmopressin, TRH, and antisense compounds.

It is believed that the present invention can be used to particular advantage in oral delivery of a composition which includes an active agent which demonstrates poor permeability across the gastrointestinal barrier in the absence of an enhancer. This includes drugs which are typically materials in solid form at room temperature and for which the particular combination of molecular weight and size, the molecular shape, the electrical charge, and the hydrophilic/lipophilic balance (HLB, defined below) of the active agent operate together to make it poorly absorbed. Examples of such bioactive materials are members of the bisphosphonates, for example, alendronate, risedronate, pamidronate, etidronate, clodronate, and tiludronic acid.

Thus, it is believed that the composition of the present invention will be used most widely with a bioactive material which is administered orally to humans and which has low bioavailability in the gastrointestinal tract of the human. The term "low bioavailability" is meant to encompass bioactive materials which are absorbed into the system of a human at an amount lower than about 20 wt. % of a dose of the bioactive material administered orally. The bioactive material may have low bioavailability because it is poorly absorbed in the gastrointestinal tract or because it is degraded in the gastrointestinal tract before absorption or by metabolism after absorption. When this is the case, a dosage form for oral administration must contain a large excess of the bioactive material to compensate for the loss. For example, when administered orally, a bioactive material which has low bioavailability such as a peptide must be administered in multiple microgram quantities, a bisphosphonate must be administered in multiple-milligram quantities, and oligionucleotide must be administered in the hundreds of milligram quantities to offset the effects of low bioavailability.

Alendronate, a bisphosphonate administered to retard bone resorption in the treatment of osteoporosis, is an example of a bioactive material which has low bioavailable. When administered orally to humans it typically has less than 1 wt. % bioavailability and is typically administered in dosages of 10 milligrams to offset its low bioavailability.

The bioactive material is present in the composition in the form of dispersed solid particles, preferably dispersed uniformly in the composition. The size of the particles can vary over a wide range. The size of the particles, as well as various parameters of the composition, have a bearing on the form in which the solid particles are present in the composition. It is believed that the mean particle size of the bioactive material will fall generally in the range of about 1 nm to about 1 mm. No particular value within that range is preferred, with the most suitable particle size being dependent upon the chemical and physical properties of the active agent being incorporated into the composition. Nevertheless, it is believed that active agents having a mean particle size of about 50 nanometers to about 500 microns will be used most widely. Mean particle size is a value arising from the measurement of a collection of variously sized particles in a manner known to those skilled in the art. The particles can be present in any suitable form, for example, as a crystalline or amorphous powder.

The bioactive material should be present in the composition in an amount such that, when presented to the desired location in the gastrointestinal tract of an animal, it results in or leads to the delivery of an amount of material which is effective in treating the involved condition. The amount of bioactive material may vary considerably, depending upon its solubility and activity, its bioavailability, the presence of a bioavailability enhancer, the use for which it is included, the nature of the patient, and the frequency of the dosage regime and other factors that are art-recognized. In general it is expected that a bioactive material will comprise between about 0.0005 and about 70 wt. % of the composition. Preferred are compositions having between about 0.005 to about 50 wt. % bioactive material.

The Encapsulating Material

In preferred embodiments of the present invention the encapsulating materials is either an enhancer or an encapsulating surfactant. Although the encapsulating surfactant may itself exhibit enhancing properties, for the purposes of the present invention, the term "enhancer" does not include the encapsulating surfactant described herein. As known, an enhancer is a material or mixture of materials that increases the bioavailability of an active agent to an animal when presented to a site of absorption with the active agent. The enhancer for use in the present invention is a material, which upon oral administration, increases absorption of a bioactive material presented to any location within the gastrointestinal tract of an animal.

The Enhancer Embodiment

The enhancer for use in the "enhancer" embodiment of the present invention, as mentioned above, is normally a solid at room temperature and has a melting point below that of the bioactive material. In formulating a composition of the present invention, the enhancer is in liquid form, and, for this reason, enhancers that melt at a temperature of 100° C. or less are preferred. It is within the scope of the present invention to formulate compositions using enhancers which are heated (melted) to achieve an acceptable form for making the composition. As the term is used herein, the term "melting" is meant to encompass both the more rigorously defined concept of melting point and the concept implied in the common sense of the word that the materials begin to liquefy. More preferred enhancers are those that have melting points of 100° C. or less, or blends of pure materials in which the pure materials have melting points of 100° C. or less.

The enhancer for use in the enhancer embodiment of the present invention exhibits hydrophobic properties. Preferably, the enhancer has a hydrophilic-lipophilic balance (HLB) value no greater than about 8 and is nonionic. The HLB value, which is a measure of the polarity of a surfactant or mixture of surfactants, is an arbitrary number defined originally for polyoxyethylene ethers as the mole percent of hydrophilic groups occurring in a molecule divided by 5. This scheme gives a hydrophilic molecule having only polar groups an HLB value of 20. For surfactant molecules other than polyoxyethylene ethers, the HLB value is derived from other physical properties in comparison to the ethers. HLB values for various materials are published. The meaning and measurement of HLB values are known in the art and are further described by Becher, et. al, *Nonionic Surfactant Physical Chemistry*, Marcel Dekker, NY 1987, pages 439-456.

Enhancers suitable for use in the enhancer embodiment of the present invention are, for example, mono-, di-, and triglyceride esters of medium-chain (more than about 6 carbon atoms in length) and long-chain (more than about 12 carbon atoms in length) fatty acids, esters of fatty acids and glycols and esters of mixed fatty acids and glycols and mixtures thereof. Other suitable enhancers include diesters of propylene glycol having from about 7 to about 55 carbon atoms, propylene glycol esters of capric and caprylic acids, and mixtures thereof, having from 19 to 23 carbon atoms. Mixtures of the above named enhancers can be used also.

Mono- and diglycerides of medium- and long-chain fatty acids have the general structure:

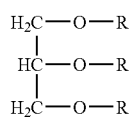

wherein at least one of "R" is a carbon moiety having 6 to about 20 carbon atoms, selected from alkyl, alkenyl, and alkyl- or alkenyl-carbonyl moieties, forming an ether bond in the case of an alkyl or alkenyl moiety and an ester bond in the case of a carbonyl moiety. For monoglycerides, both of the remaining "R" moieties are hydrogen. For diglycerides, one of the remaining "R" groups is hydrogen and the other is a carbon moiety having at least 6 carbon atoms selected to be the same or different, for each occurrence, from alkyl, alkenyl, and alkyl- or alkenyl-carbonyl groups.

A preferred enhancer is a mono or diglyceride of caprylic acid, a mono or diglyceride of capric acid, or a mono or di-glyceride of a mixture of capric and caprylic acids, or a mixture of two or more thereof.

As described in detail below in connection with the description of a preferred method for preparing the composition of the present invention, solid particles of the bioactive material are mixed into and dispersed in a molten form of the enhancer and remain dispersed as the molten form of the enhancer solidifies upon cooling. Upon solidification, the enhancer exists in the composition as a continuous solid phase in which the solid particles of bioactive material are dispersed and encapsulated.

The enhancer is used to particular advantage when the bioactive material has poor bioavailability; it is used in an amount at least sufficient to improve the absorption of the bioactive material. The amount of enhancer used will depend on various factors, including, for example, the particular enhancer and the identity, form and amount of bioactive material present in the composition. For guideline purposes, it is suggested that the composition include at least about 5 wt. % of the enhancer. It is believed that for most applications the amount of enhancer will generally comprise about 5 to about 99 wt. % of the composition. In preferred form, the enhancer comprises from about 10 to about 80 wt. % of the composition and most preferred about 20 to about 75 wt. % of the composition.

In a preferred form, the enhancer embodiment of the present invention includes also a block copolymer, as described below. The block copolymer should be present in an amount sufficient to provide a solid composition with rapid onset of release of the bioactive material contained therein. It is recommended that the block copolymer be used in an amount of about 10 wt. % to about 50 wt. % of the composition, preferably in an amount of about 10 wt. % to about 40 wt. % of the composition.

The Encapsulating Surfactant Embodiment

The encapsulating surfactant embodiment of the present invention includes in the composition a polyoxyethylene/polyoxypropylene block copolymer that is normally a solid at room temperature, that is nonionic in nature, and has an HLB of at least about 13. A preferred block copolymer is a non-ionic, tri-block-structured copolymer of polyoxyethylene and polyoxypropylene which has the general structure:

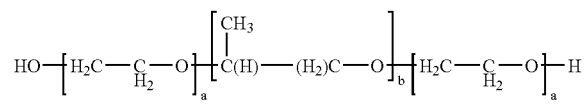

where "a" and "b" represent a polymeric number of repeating structural units and indicate that the polyoxyethylene terminal end blocks are an equal number of repeating units, while the center polyoxypropylene block may have the same or a different number of repeating structural units. Such a block copolymer has surface active properties and is known in various arts as a poloxamer block copolymer (for convenience, also referred to herein as a "poloxamer").

It will be appreciated that the polyoxyethylene blocks which comprise the terminal portions of these polymers is hydrophilic whilst the polyoxypropylene block which comprises the center portion of these polymers is hydrophobic. Accordingly, the poloxamer may have a wide range of surface active properties depending upon the molecular weight of each block and the ratio of the weights of the polyoxyethylene and polyoxypropylene blocks. Particularly suitable poloxamers are those having a molecular weight between about 6000 and about 15,000, and which have an HLB value of at least 13. Most preferred are poloxamers having a molecular weight between about 7000 and about 10,000 and an HLB value of between about 25 and about 35. Commercially available poloxamers suitable for use in compositions of the present invention are, for example, Lutrols (available in Europe), for example, Lutrol F68, and Pluronics (BASF), for example, Pluronic F68.

The block copolymer is present in the composition in an amount at least sufficient to produce the desired effect. The amount used will depend on various factors, including, for example, the particular copolymer used, the identity, form and amount of bioactive material, and/or optimal ingredients (for example, an enhancer) present in the composition. For guidelines purposes, it is suggested that the composition include at least about 10 wt. % of the block copolymer. It is believed that for most applications the amount of block copolymer will generally comprise about 10 to about 50 wt. % of the composition. In preferred form, the composition comprises from about 10 to about 40 wt. % of the block copolymer.

In preferred form, the encapsulating surfactant embodiment of the present invention includes also an enhancer, preferably a mono or diglyceride of caprylic acid, a mono or diglyceride of capric acid, or a mono or diglyceride of a mixture of capric and caprylic acids, or a mixture of two or more thereof. The enhancer included in the composition of the block copolymer embodiment can be a liquid, but preferably is a solid at room temperature. If a liquid enhancer is used, it should be present in an amount which does not interfere with the formation of the solid pharmaceutical composition of the composition. The enhancer should be present in an amount sufficient to improve the absorption of the bioactive material within the gastrointestinal tract of the animal. It is recommended that the enhancer be used in an amount of about 10 wt. % to about 75 wt. % of the composition, preferably an amount of about 20 wt. %. to about 75 wt. % of the composition.

Optional Ingredients

Each of the embodiments of the composition of the present invention can include optional ingredients, as exemplified below.

The embodiments of the present invention include preferably another surfactant or a mixture of two or more surfactants. Such surfactant(s) can perform various functions. For example, a surfactant can function to aid in maintaining the solid particles of active agent dispersed in the composition and/or act as a permeation enhancer. A surfactant can act as a permeation enhancer by functioning to remove the mucous coating on the surface of a membrane through which a bioactive material is to be delivered. This permits more facile access to the membrane by the active agent.

Another role which is exemplary of the additional surfactant's function in the composition is to improve wettability or dispersibility of the delivery system. In this role, the surfactant aids in breaking up the composition in the presence of an aqueous phase to release the bioactive material and enhancer/ block copolymer contained in the composition. In terms of use of the composition of the present invention, such an environment is found in the gastrointestinal tract in which the surfactant can act to facilitate the dispersion of the bioactive material when released to the gastrointestinal tract. It can also improve the rate of ingress of water from the gastrointestinal tract into the composition, facilitating release of the drug from the composition.

An additional surfactant can also act to facilitate the formation of mixed micelles when the composition is released in the gastrointestinal tract. Mixed micelles can aid in solubilization of bioactive materials when they are released in the gastrointestinal tract. Mixed micelles can also potentially enhance bioavailability of orally administered bioactive materials by preventing or suppressing enzymatic degradation of the bioactive material through the formation of a surface layer that prevents enzymatic degradation of certain bioactive materials.

The additional surfactant should have an HLB of about 9 to about 20, preferably to about 10 to about 18. Such surfactants can be a solid, semi-solid, or a liquid at room temperature. They can be nonionic or ionic, that is, anionic, cationic, or zwitterionic. A mixture of nonionic and ionic surfactants can be used. Preferably, the additional surfactant is a nonionic surfactant.

Examples of non-ionic surfactants which may be employed are ethoxylated castor oil; ethoxylated derivatives of $C_{5-29}$ mono-glycerides; polyoxyethylene derivatives of $C_{15-60}$ diglycerides having 1 to 90 oxyethylene (POE) repeating units; $C_{8-96}$ ethoxylated fatty esters; $C_{14-130}$ sucrose fatty esters; and polyoxyethylene derivatives of $C_{20-130}$ sorbitol and sorbitan monoesters and triesters having 0 to 90 POE repeating units, e.g., polyoxyethylene sorbitan monooleate, sorbitol hexaoleate POE (50). Additionally, polyglycolized polyglycerides such as Gelucire 50/13 and Gelucire 44/14 can be used.

Examples of anionic surfactants include salts of $C_{8-32}$ fatty acids; derivatives of cholic acid, for example, deoxycholate salts, ursodeoxycholate salts, and taurocholate salts; and sodium lauryl sulfate (SLS).

Examples of cationic surfactants include cetyldimethylethylammonium bromide, cetylpyridinium chloride, cetyltrimethyl ammonium bromide, and other salts of these surfactants.

Preferred "additional" surfactants for use in the composition of the present invention are polyoxyethylene castor oil derivatives, polyoxyethylene stearates, polyglycolysed glycerides, for example lauroyl macrogol-32 and steroyl macrogol-32 glycerides, and polyoxyethylene sorbitan fatty acid esters. A particularly preferred additional surfactant is a polyoxyethylene sorbitan monooleate.

In those embodiments in which a "additional" surfactant is used, it should be present in an amount of about 0.01 wt. % to about 20 wt. % of the composition, preferably about 1 to about 15 wt. % of the composition.

A biocompatible oil may be incorporated into the composition to aid, for example, in formation of a suspension of the solid active agent in the melted enhancer. Some biocompatible oils may also act to increase the efficacy of the enhancer. Additionally, a biocompatible oil may be added to facilitate the formation of an oil-in-water emulsion in the gastrointestinal tract. Incorporation of the oil in the composition is believed to facilitate the formation of an oil-in-water emulsion upon introduction of the composition into the aqueous environment of the gastrointestinal tract. For certain bioactive materials, the emulsion can deter in the environment of the gastrointestinal tract the degradation of the bioactive material. Reducing the amount of the bioactive material degraded increases the amount available for absorption and consequently its bioavailability.

Suitable biocompatible oils include, for example, triesters of glycerol having from about 9 to 83, preferably about 20 to about 60, and more preferably about 21 to about 45 carbon atoms. The triglycerides are further exemplified as short-chain compounds having about 9 to about 15 carbon atoms, medium-chain triglycerides having about 21 to about 45 carbon atoms, and long-chain triglycerides having above 45 carbon atoms. Short-chain and medium-chain triglycerides are preferred. Examples of glycerol triesters include natural, edible oils such as canola, corn, olive, sunflower and coconut oils, triacetin, the decanoic acid esters, and chemically-synthesized oils such as 1-oleyl-2,3-diacetyl glycerol. Commercially available triglyceride oils, both natural and chemically-synthesized, are available from Karlshamns Lipid Specialties, USA as the Captex® series, and from Huls America Inc. as the Miglyol® series.

The amount of oil added to composition is dependent upon the nature of the bioactive material incorporated into the composition, factors such as the amount and nature of the other surface active constituents and other art known factors. The composition can comprise from about 0.1 wt. % to about 50 wt. % of a biocompatible oil, preferably about 1 wt. % to about 25 wt. %.

A thickener may be included in the composition to increase the viscosity thereof Increasing the viscosity of the composition can help maintain the dispersion of the solid particles of the active agent in the liquid suspension, as may be desired. Examples of thickeners which can be used are colloidal silica, polyethylene glycol, and poly(vinyl pyrrolidone). When used, a thickener will comprise typically about 0.1 wt. % to about 50 wt. % of the composition, preferably about 0.5 wt. % to about 40 wt. %.

In preferred form, the composition is water-free, or substantially water-free, that is, no greater than about 5 wt. % water. Optionally, sparing amounts of water can be added to the composition if needed to aid in forming a suspension of certain of the active agents. Water may also be added to aid in the incorporation of certain surfactants into the composition, for example, surfactants that will later participate in the formation of protective oil-in-water emulsions when compositions of the present invention are present in the aqueous environment of the gastrointestinal tract. When used, the water will comprise typically 0.1 wt. % to about 10 wt. % of the composition.

Optionally, other materials may be added to the composition to modify its performance in the system of an animal, its handling properties, and/or its storage properties. Examples of such optional components are gelling agents, stabilizers to maintain the potency of the bio-active material in storage, flavoring and colorants to impart desirable taste and appearance to the composition, plasticizers and preservatives.

The composition of the present invention can be made by an suitable process which will result in a composition in which solid particles of the bioactive material are dispersed and encapsulated by the encapsulating material, for example, the enhancer and/or encapsulating surfactant. In preferred form, the encapsulating material is heated to a temperature sufficiently high to melt and liquefy it. Solid particles of the bioactive material are added to the liquified encapsulating material and mixed therein to distribute them uniformly in the liquified encapsulating material to form a liquid mixture in which the solid particles of bioactive material are dispersed. In preferred form, other ingredients are included in the liquified encapsulating material prior to adding thereto the solid particles of bioactive material. The liquid mixture is cooled to room temperature and the encapsulating material solidifies to form a continuous solid phase in which the solid particles of bioactive material are dispersed and encapsulated. In a preferred embodiment which comprises forming capsules filled with the composition of the present invention, individual capsules are filled with the aforementioned liquid mixture which solidifies in the capsule as the mixture cools. It should be appreciated that the preferred process for preparing the composition of the present invention involves the use of heat to convert the solid encapsulating material to a liquid and that it is not necessary to use a solvent for the encapsulating material. Accordingly, the encapsulating material solidifies as it is cooled and not by virtue of the evaporation of a solvent therefor. It should be appreciated also that the liquid mixture may contain a liquid solvent for one or more of other constituents included in the mixture, but the nature of the solvent and/or amount present does not interfere with the ability of the liquid mixture to solidify as it cools.

The composition of the present invention can be directly orally administered or can be contained in any delivery vehicle that is convenient for oral administration for delivery of the bioactive material to the gastrointestinal tract of an animal. As is known, certain bioactive materials are preferably delivered to specific sites of the gastrointestinal tract, either to achieve maximum bioavailability of the bioactive material or to effect treatment of specific regions or membranes of the gastrointestinal tract. Accordingly, a vehicle which contains the composition of the present invention may bear a coating, for example, an enteric coating, insuring that the bioactive material is released at the most advantageous location in the gastrointestinal tract.

Delivery vehicles suitable for oral administration are, for example, hard and soft gelatine capsules, hydroxypropyl methyl cellulose (HPMC) capsules, starch capsules, and tablets, the latter being employed when compositions of the present invention can be incorporated into a solid media, whether by absorption or adsorption, or otherwise stabilized in a media that permits incorporation into a pressed tablet. Hard or soft gelatin capsules are particularly suited as vehicles for oral delivery of the composition of the present invention. Enteric coatings which may be used are well known in the art. Such coatings can be formulated to degrade or dissolve at a particular location in the gastrointestinal tract, thereby delivering their contents to a given portion of the gastrointestinal tract. Examples of materials which can be used to coat vehicles include polyacrylic and methacrylic acid polymers and hydroxypropylmethylcellulose phthalates. Examples of such materials are the Eudragit L, S, and FS-30D coating materials and mixtures thereof; they are commercially available from Rohm GmbH.

EXAMPLES

Examples below are illustrative of compositions of the present invention. A comparative example is set forth also. The bioactive material used in all of the compositions of the examples is alendronate monosodium trihydrate (hereafter "alendronate") in micronized form. The compositions are suitable for oral administration of alendronate to an animal in need of a therapy that requires systemic administration of bisphosphonate. The proportions of constituents of the exemplary compositions are expressed as weight percent of the total weight of the composition.

Table 1 contains examples of compositions of the present invention illustrating the use of various enhancers (Examples 1 and 2) and of a surfactant (Example 3) that can be used as an encapsulating material in accordance with the present invention. Each of the encapsulating materials identified in Table 1 is a solid material at room temperature which has a melting point below the melting point of alendronate. In each of the compositions, alendronate is present in the composition in the form of a dispersed powder.

TABLE 1

| Ex. No. | Enhancer | Enhancer, wt. % | Alendronate, wt. % |
|---|---|---|---|
| 1 | Capmul ® MCM (glyceride esters of medium chain fatty acids) | 97.20 | 2.80 |
| 2 | Capmul ® MCM C10 (mono- and diglyceride esters of capryic acid) | 98.33 | 1.67 |
| 3 | Lutrol ® F68 (tri-blockpolyoxyethylene/ polyoxypropylene copolymer surfactant) | 97.20 | 2.80 |

Each of the compositions identified in Table 1 is prepared by heating the encapsulating material to its melting point to liquefy it and then adding the alendronate. Thereafter, the mixture was stirred until homogeneous and allowed to cool to ambient temperature, forming a solid with particles of alendronate dispersed throughout.

The next group of examples (Nos. 4 to 6) is illustrative of solid compositions of the present invention which are capable of rapidly releasing the bioactive material of the composition. In all of the compositions, the encapsulating material includes both a polyoxyethylene/polyoxypropylene block copolymer (Lutrol F68®) encapsulating surfactant and an enhancer (Capmul® MCM). The compositions are prepared by formulating a base composition comprising an enhancer, the block copolymer encapsulating surfactant, an oil, propylene glycol, and a second surfactant, followed by addition of the alendronate. The constituents comprising the composition and the amounts thereof are set forth below in Table 2.

TABLE 2

| Example No. | Encapsulating Surfactant, (Lutrol 68 ®) g/wt. % | Oil (Captex 355 ®) g/wt. % | Time for release of 80% of assayed bioactive material (dissolution test) | Stability (change after 4 weeks) |
|---|---|---|---|---|
| 4 | 89 g/17.8% | 111.5 g/22.3% | <30 min | Unchanged (stable) |
| 5 | 111.5 g/22.3% | 89.0 g/17.8% | <30 min | Unchanged (stable) |
| 6 | 133.5 g/26.7% | 67 g/13.4% | ~30 min | Unchanged (stable) |

*In addition to the above-identified surfactant and oil, each of the compositions contained 49.0 wt % Capmul MCM ® (enhancer), 4.5 wt % Tween 80 ® (second surfactant), 2.8 wt % propylene glycol, and 3.6 wt % alendronate monosodium trihydrate (alendronate, bioactive material).

The aforementioned base composition was prepared by melting 245 g of the Capmul® MCM (enhancer) in a 37° C. water bath and stirring into it 22.5 g of Tween® 80 (second surfactant) and 14 g of the propylene glycol. Next, the Captex 355® (biocompatible oil) was added along with polyoxyethylene/polyoxypropylene encapsulating surfactant (Lutrol F68®). After the addition of the encapsulating surfactant, the temperature of each of the mixtures was raised to about 55° C. and stirring and heating were continued until the mixtures were homogeneous.

Each mixture (in the form of a warm, viscous liquid) was transferred to an IKA vessel fitted with two homogenizers and a stirring paddle. Into the vessel were added 18 g of the (alendronate) in the form of a micronized powder. Addition was carried out with the stirrer running at about 35 rpm and the homogenizers running at 8000 rpm. After the alendronate was added, stirring and homogenization of each of the mixtures were continued for an additional 15 minutes. After 15 minutes of continued stirring and homogenizing, each mixture was in the form of a homogeneous viscous liquid with alendronate micronized powder uniformly distributed throughout.

Each of the mixtures was cooled to about 35° C. at which temperature the mixture was in the form of a highly viscous, white liquid. Random samples from this viscous liquid mass were obtained for each of these compositions. The random samples were cooled and assayed for uniformity of alendronate content. The assays indicated that the uniformity content of the alendronate throughout the mass of each of the mixtures was within a range acceptable for pharmaceutical preparations.

After sampling for uniformity, a portion of each of the final compositions of the examples of Table 2 was injected into airfill capsules and cooled to ambient temperature, forming a solid comprising the composition within the capsule. The capsules were tested for dissolution characteristics using a USP II apparatus equipped for carrying out dissolution study using the "paddles" method. The study was carried out using deionized water as the dissolution media at 37.5° C. and paddles operating at 50 rpm. Dissolution studies were performed on capsules prepared according to the above description both contemporaneously with cooling to ambient temperature (within 24 hours after solidification) and after storage at ambient temperature for four weeks. The results are summarized in Table 2 above. In carrying out the dissolution studies, the dissolution media was sampled in 15 minute intervals and assayed for alendronate content. An 80% release of the bioactive material from the composition in "<30" indicates that, at the 30 minute observation, more than 80% release of the material was measured, while a report of "~30" indicates that at 30 minutes the sample contained an amount of the bioactive material corresponding to about 80% release.

For stability studies, the bulk viscous liquid remaining after the preparation of capsules for each example composition was allowed to solidify in a sealed vessel at ambient temperature. The solid was stored at room temperature and observed for indications of instability, for example, settling of the suspended alendronate, solids dropping to the bottom of the vessel, and/or the appearance of liquid separating from the bulk of the sample. The example compositions remained solid with no observable changes, thus indicating that all compositions were stable. The results are summarized also in Table 2 above.

The next group of examples is illustrative of the role which can be played by the encapsulating surfactant of the present invention in providing a solid composition. In Table 3, below, are illustrated a composition of the present invention (Example No. 7) comprising a polyoxyethylene/polyoxypropylene block copolymer (Lutrol F68®) as an encapsulating surfactant, an alendronate powder, an oil (Captex 355®), an enhancer (Capmul MCM®), and a second surfactant (Tween 80®). Comparative Example A comprises the same materials in the same proportion as Example 1, except that a polyglycolized glyceride surfactant (Gelucire 50/13®) has been substituted for the encapsulating surfactant of the present invention. The compositions of Example 7 and Comparative Example A were prepared according to the method used to prepare the compositions of Examples Nos 4 to 6; described above. The compositions and the properties of the compositions are reported in Table 3.

TABLE 3

| Composition (g/wt %) | Example No. 7 | Comparative Example A |
|---|---|---|
| Tween 80 ® surfactant | 22.5 g/4.5% | 22.5 g/4.5% |
| propylene glycol | 14.0 g/2.8% | 14.0 g/2.8% |
| Alendronate MSTH* | 18.0 g/3.6% | 18.0 g/3.6% |
| Lutrol F68 ® surfactant | 111.5 g/22.3% | — |
| Gelucire 50/13 ® surfactant | — | 111.5 g/22.3% |
| Captex 355 ® oil | 44.5 g/8.9% | 44.5 g/8.9% |
| Capmul MCM ® enhancer | 289.5 g/57.9% | 289.5 g/57.9% |
| Time for Release of 80% of alendronate (dissolution test) (min) | ~30 min | ~30 min |
| Stability (change after 4 weeks) | Stable (no change) | Unstable (viscous liquid, oil separates out) |

Upon cooling, the composition of Example No. 7, containing the Lutrol F68® surfactant, was a white solid and that of Comparative Example A, containing the Gelucire 50/13® surfactant, was a white viscous liquid.

Before cooling, the compositions of the Example 7 and Comparative Example A were used to prepare capsules containing the compositions, as described above for Example Nos. 4 to 6. The capsules were tested, as described above, for alendronate-release properties contemporaneously upon cooling (within 24 hours) and after storage under ambient conditions for four weeks. Samples of the bulk material of each of the compositions were stored for four weeks under ambient conditions and examined for evidence of instability according to the procedure described above. The composition of Example 7 remained a solid and showed no evidence of instability, but the composition of comparative Example A indicated that variation in alendronate content of the bulk materials of both of these examples was within a range acceptable for pharmaceutical preparations.

Before solidification, capsules containing these compositions were prepared as described above for Examples 4-6. The capsules were tested, as described above, for bioactive material release properties contemporaneously upon cooling (within 24 hours) and after 12 days of storage under ambient conditions. The bulk material was stored for two weeks under ambient conditions and examined for evidence of instability according to the procedure described above. Both example compositions remained solid and showed no signs of instability. The results of the stability comparison and bioactive material release rates are also reported in Table 4, below.

TABLE 4

| Example No. | Amount of Lutrol F68 ® g/wt % of total composition* | Amount of PEG 1000 g/wt % of total composition* | Time for Release of 80% of Assayed Bioactive Material (dissolution test) (min) | Stability (change after 2 weeks) |
|---|---|---|---|---|
| 8 | 89.2 g/17.82% | 44.6 g/8.92% | <30 min | Unchanged (stable) |
| 9 | 66.85 g/13.37% | 66.85 g/13.37% | <30 min. | Unchanged (stable) |

*Balance of composition is: Capmul MCM ®, 48.99 wt %; Captex 355 ®, 13.37 wt %; Tween 80 ®, 4.45 wt %; propylene glycol, 2.81 wt %; and alendronate, 3.66 wt % showed separation of oil from the sample and was, therefore, unstable. The results of the stability comparison and alendronate-release rates are reported in Table 3 above.

It is expected that the liquid composition of comparative Example A would have a rapid onset of release, as is observed. The examples in Table 3 illustrate that solid compositions which are stable can be prepared according to the present invention which have rapid onset release profiles equal to those obtained from comparably formulated and unstable liquid compositions, and that advantageously, the use of polyethyleneoxide/polypropyleneoxide block copolymers, for example, Lutrol F68®, provide compositions which display both rapid onset of release and are solid, stable composition.

The next two examples are illustrative of solid compositions of the present invention; comprising an enhancer, an encapsulating surfactant, an oil, propylene glycol, a second surfactant, alendronate and polyethylene glycol in the form of PEG-1000. The proportions of the constituents of Example Nos. 8 and 9 are similar to those of the composition of Example No. 6, except that a portion of the encapsulating surfactant used in the composition of Example No. 6 (Lutrol F68®) is replaced with polyethylene glycol (PEG-1000). Examples 8 and 9 were prepared following the procedure described above for Example Nos. 4 to 7. Examples 8 and 9 comprise 245 g of an enhancer (Capmul MCM®, ~49 wt %), 22.5 g of a second surfactant (Tween 80®, ~4.5 wt. %), 66.8 g of an oil (Captex 355®, ~13.4 wt %), 14.1 g of propylene glycol (~2.81 wt %), 18.3 g of a bioactive material (alendronate, ~3.66 wt %), and an encapsulating surfactant (Lutrol F68®) and PEG 1000 in the amounts, and representing the weight percentage of the composition, shown in Table 4, below.

The compositions of both Examples 8 and 9 were white solids. Random samples from the mass of each of these compositions were obtained. The random samples of the compositions were assayed according to the above-described procedure for uniformity of alendronate content. The assays The above examples demonstrate that compositions of the present invention may be formulated to be stable suspensions of powdered bioactive materials by virtue of their solid nature. They also demonstrate that these solid compositions retain the ability to provide rapid onset release of the powder contained within the composition.

It will be appreciated that the powdered bioactive material used in the example formulations described above can be present in an instant release form, a delayed release form, or a mixture of the two.

The invention claimed is:

1. A solid oral pharmaceutical composition which consists essentially of: (A) about 0.0005 to about 70 wt. % of a pharmaceutically effective amount of solid particles of a water-soluble bioactive material which is a bisphosphonate and which has a low bioavailability in the gastrointestinal tract of an animal and which is a solid at room temperature and which has a predetermined melting point; (B) about 5 to about 80 wt. % of a glyceride enhancer which is normally a solid at room temperature and which has a melting point lower than the melting point of the bioactive material and which is present in an amount that increases the bioavailability of the bioactive material when it is present within the gastrointestinal tract of an animal; (C) about 10 to about 50 wt. % of a polyoxyethylene/polyoxypropylene block copolymer surfactant; and optionally (D) about 0.01 to about 20 wt. % of another surfactant which has an HLB of about 9 to about 20 and/or about 0.1 to about 50 wt. % of a biocompatible oil; wherein the enhancer is present in the composition in the form of a continuous solid phase in which the solid particles of bioactive material are dispersed uniformly and encapsulated in the composition, wherein the composition is stable, and wherein the solid particles have a mean particle size of about 1 nm to about 1 mm.

2. The composition according to claim 1 including also about 0.01 to about 20 wt. % of another surfactant which has an HLB of about 9 to about 20.

3. The composition according to claim 1 including also about 0.1 to about 50 wt. % of a biocompatible oil.

4. The composition according to claim 1 wherein said glyceride enhancer consists essentially of a mono- or di-glyceride of capric acid, a mono- or di-glyceride of caprylic acid, or a mixture of mono- and di-glycerides of caprylic and capric acids, or a mixture of two or more thereof, and said block copolymer has a molecular weight of about 6000 to about 15,000 and an HLB value of at least about 13.

5. The composition according to claim 1, wherein the solid particles have a mean particle size of about 50 nm to about 0.5 mm.

* * * * *